(12) United States Patent
Bauer et al.

(10) Patent No.: US 9,675,268 B2
(45) Date of Patent: Jun. 13, 2017

(54) DETECTION AND DIFFERENTIATION OF SLEEP DISORDERED BREATHING

(75) Inventors: Peter T. Bauer, West Linn, OR (US); Marco Dalla Gasperina, Vancouver, WA (US); Patricia A. Arand, McMinnville, OR (US); Timothy K. Wheeler, Portland, OR (US)

(73) Assignee: Inovise Medical, Inc., Beaverton, OR (US)

( * ) Notice: Subject to any disclaimer, the term of this patent is extended or adjusted under 35 U.S.C. 154(b) by 66 days.

(21) Appl. No.: 12/940,293

(22) Filed: Nov. 5, 2010

(65) Prior Publication Data

US 2011/0105915 A1    May 5, 2011

Related U.S. Application Data

(60) Provisional application No. 61/280,558, filed on Nov. 5, 2009.

(51) Int. Cl.
*A61B 5/08* (2006.01)
*A61B 5/0456* (2006.01)
(Continued)

(52) U.S. Cl.
CPC .......... *A61B 5/0456* (2013.01); *A61B 5/1135* (2013.01); *A61B 5/4806* (2013.01);
(Continued)

(58) Field of Classification Search
CPC ..... A61B 5/0205; A61B 5/0452; A61B 5/021; A61B 5/1135; A61B 7/04; A61B 7/003
See application file for complete search history.

(56) References Cited

U.S. PATENT DOCUMENTS

| 5,392,780 | A | 2/1995 | Ogino et al. |
| 5,758,654 | A | 6/1998 | Burton-Krahn et al. |

(Continued)

FOREIGN PATENT DOCUMENTS

CA    1256507    6/1989

OTHER PUBLICATIONS

International Search Report, Serial No. PCT/US10/055696, dated Dec. 23, 2010, 13 pages total.

(Continued)

*Primary Examiner* — Michael Kahelin
*Assistant Examiner* — Tho Tran
(74) *Attorney, Agent, or Firm* — Kolisch Hartwell, P.C.

(57) ABSTRACT

A vector method for monitoring a subject's sleep-disordered breathing utilizing a single, anatomy-attached (anatomically outside or implanted inside), three-orthogonal-axis accelerometer(s), including the steps of (1) collecting from a sleeping subject three-orthogonal-axis data relating to at least one of sound data, subject posture, subject activity, snoring, and respiration, and (2) following such collecting, processing and analyzing collected data to detect associated, disordered breathing including assessing the presence of at least one of (a) sleep-disordered breathing generally, (b) sleep apnea specifically, and (c) differentiation between central and obstructive sleep apnea. Further involved is the acquiring of ECG data, and that the mentioned processing and analyzing include recognition of such acquired ECG data.

2 Claims, 9 Drawing Sheets

Figure 1:
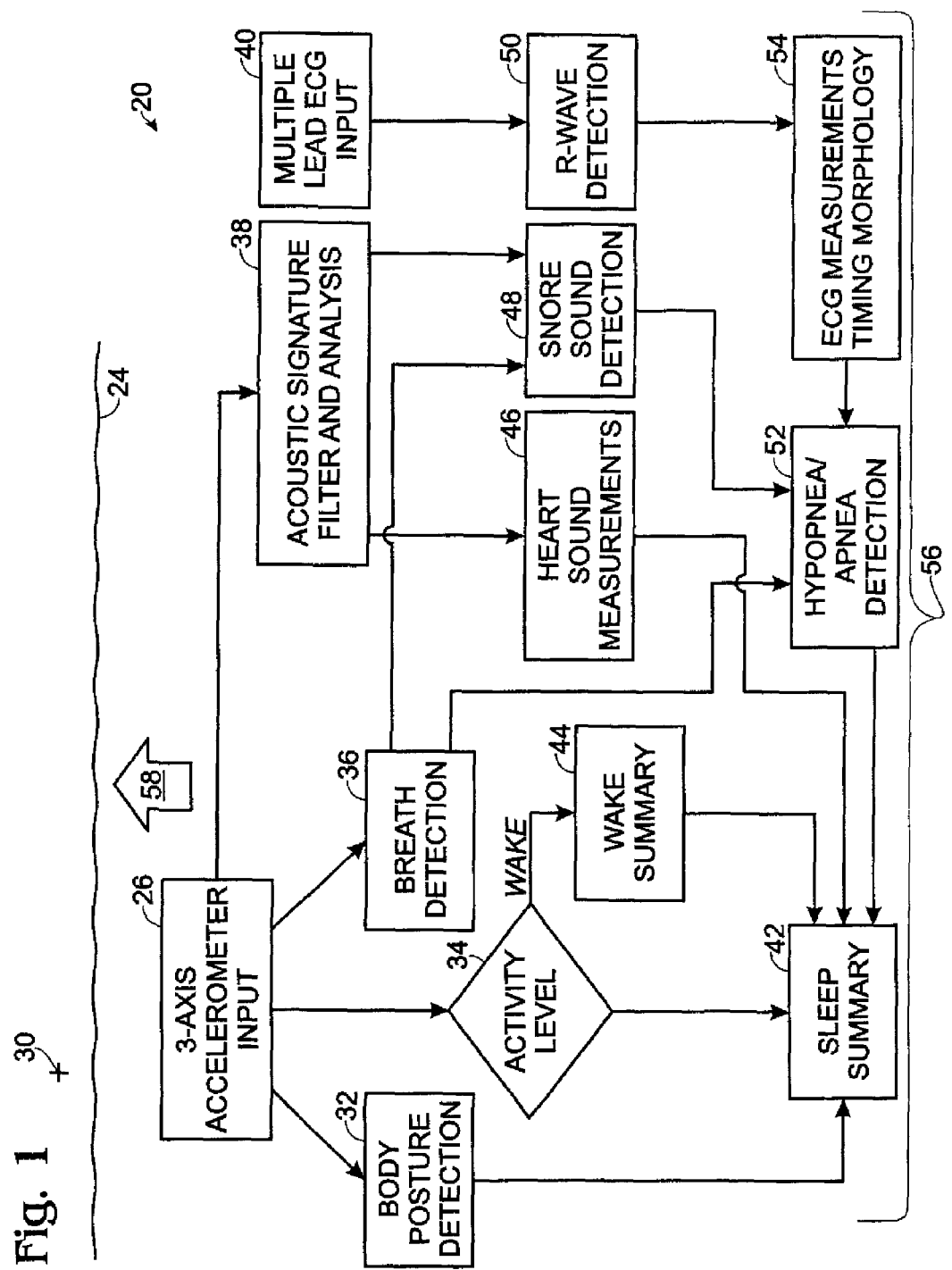

(51) Int. Cl.
    *A61B 5/113*     (2006.01)
    *A61B 5/00*     (2006.01)
    *A61B 7/00*     (2006.01)
    *A61B 5/11*     (2006.01)

(52) U.S. Cl.
    CPC .......... *A61B 5/4809* (2013.01); *A61B 5/4818* (2013.01); *A61B 7/003* (2013.01); *A61B 5/1116* (2013.01); *A61B 5/1118* (2013.01); *A61B 2562/0219* (2013.01)

(56) References Cited

U.S. PATENT DOCUMENTS

| | | |
|---|---|---|
| 7,039,538 B2 | 5/2006 | Baker, Jr. |
| 7,074,195 B2 | 7/2006 | Nelson et al. |
| 7,096,060 B2 | 8/2006 | Arand et al. |
| 7,113,820 B2 | 9/2006 | Schlegel et al. |
| 7,171,269 B1 | 1/2007 | Addison et al. |
| 7,174,203 B2 | 2/2007 | Arand et al. |
| 7,225,021 B1 | 5/2007 | Park et al. |
| 7,248,923 B2 | 7/2007 | Maile et al. |
| 7,302,290 B2 | 11/2007 | Bauer |
| 7,357,775 B1 | 4/2008 | Koh |
| 7,424,321 B2 | 9/2008 | Wariar et al. |
| 7,431,699 B2 | 10/2008 | Siejko et al. |
| 7,467,012 B1 | 12/2008 | Park et al. |
| 7,559,903 B2 | 7/2009 | Moussavi et al. |
| 7,725,181 B1* | 5/2010 | Bornzin et al. ............ 607/9 |
| 7,819,814 B2 | 10/2010 | Gavriely et al. |
| 8,105,241 B2 | 1/2012 | Nelson et al. |
| 8,137,283 B2 | 3/2012 | Syeda-Mahmood et al. |
| 2002/0188329 A1 | 12/2002 | Struble |
| 2003/0187337 A1 | 10/2003 | Tarassenko et al. |
| 2004/0127792 A1 | 7/2004 | Siejko et al. |
| 2004/0230105 A1 | 11/2004 | Geva et al. |
| 2005/0027323 A1 | 2/2005 | Mulligan et al. |
| 2005/0043644 A1* | 2/2005 | Stahmann et al. ............ 600/529 |
| 2005/0065563 A1 | 3/2005 | Scheiner |
| 2005/0080348 A1* | 4/2005 | Stahmann et al. ............ 600/529 |
| 2005/0085865 A1 | 4/2005 | Tehrani |
| 2005/0090870 A1 | 4/2005 | Hine et al. |
| 2005/0119711 A1* | 6/2005 | Cho et al. ............ 607/42 |
| 2005/0222515 A1 | 10/2005 | Polyshchuk et al. |
| 2006/0079942 A1 | 4/2006 | Deno et al. |
| 2006/0155202 A1 | 7/2006 | Arand et al. |
| 2007/0038137 A1 | 2/2007 | Arand et al. |
| 2007/0055151 A1 | 3/2007 | Shertukde et al. |
| 2007/0073181 A1* | 3/2007 | Pu ............ A61B 5/0816 600/529 |
| 2007/0191725 A1 | 8/2007 | Nelson |
| 2008/0021510 A1 | 1/2008 | Mi et al. |
| 2008/0125820 A1 | 5/2008 | Stahmann et al. |
| 2008/0177191 A1 | 7/2008 | Patangay et al. |
| 2008/0255465 A1 | 10/2008 | Nelson |
| 2009/0024176 A1 | 1/2009 | Yun et al. |
| 2009/0112107 A1 | 4/2009 | Nelson et al. |
| 2009/0112108 A1 | 4/2009 | Nelson et al. |
| 2009/0165559 A1 | 7/2009 | Lec |
| 2010/0094148 A1 | 4/2010 | Bauer et al. |
| 2010/0217345 A1* | 8/2010 | Wolfe et al. ............ 607/17 |
| 2010/0331903 A1 | 12/2010 | Zhang et al. |
| 2011/0015702 A1* | 1/2011 | Ternes et al. ............ 607/62 |
| 2012/0296228 A1 | 11/2012 | Zhang et al. |
| 2012/0296388 A1 | 11/2012 | Zhang et al. |
| 2013/0030484 A1 | 1/2013 | Zhang et al. |

OTHER PUBLICATIONS

USPTO Office Action, U.S. Appl. No. 12/315,165, dated Nov. 12, 2010, 9 pages total.

USPTO Office Action, U.S. Appl. No. 11/264,328, dated May 9, 2008, 7 pages total.

USPTO Office Action, U.S. Appl. No. 11/264,328, dated Oct. 16, 2008, 8 pages total.

USPTO Office Action for U.S. Appl. No. 12/321,646 dated Jun. 17, 2011. 9pp.

USPTO Office Action for U.S. Appl. No. 12/288,712 dated Apr. 11, 2011. 5pp.

USPTO Office Action for U.S. Appl. No. 12/321,647 dated Jun. 1, 2011. 7pp.

USPTO Office Action for U.S. Appl. No. 12/321,650 dated Sep. 7, 2011. 8 pp.

USPTO Office Action for U.S. Appl. No. 12/005,555 dated Dec. 23, 2010. 7pp.

* cited by examiner

DETECTION AND DIFFERENTIATION OF SLEEP DISORDERED BREATHING

CROSS REFERENCE TO RELATED APPLICATION

This application claims filing-date priority to currently copending U.S. Provisional Patent Application Ser. No. 61/280,558, filed Nov. 5, 2009, for "Detection and Differentiation of Sleep Disordered Breathing Patterns". The entire disclosure content of this prior-filed provisional application is hereby incorporated herein by reference.

BACKGROUND AND SUMMARY OF THE INVENTION

This invention relates (a) to the detection of sleep-disordered breathing, (b) to the differentiation of its various manifestations and to their timing and prevalence of occurrence, and (c) to associated cardiovascular impact. In this important health-assessment setting and field, the invention particularly features, for such detection and differentiation purposes, the novel use of an anatomy-attached, three-orthogonal-axis accelerometer as the principal agency for acquiring, in simultaneity, certain key, mechanical, multi-facet anatomical information, featuring highly-persuasive, three-dimensional, vector information, which is fundamentally relevant to finding and characterizing disordered breathing. The use of such an accelerometer has been discovered by us to yield data which, at least in part because of its three-dimensional vector nature, in relation to the best known prior art practices in this area, significantly improves the critical, detection and differentiation medical focus on, and understanding of, a multifaceted breathing condition which is serious, often elusive, and in some undetected and unmanaged circumstances, fatal.

Sleep disordered breathing is a condition characterized by repeated episodes of underbreathing (hypopnea) and not breathing (apnea). It is believed that a significant population of adults experience sleep-disordered breathing.

There are two main forms of sleep apnea—central and obstructive. Central sleep apnea is related to a dysfunction of the autonomous nervous system that reduces respiratory drive, and which can lead to long breathing pauses. Obstructed airway paths cause obstructive sleep apnea. The differential diagnosis of both forms of apnea is non-trivial, and multiple vital signs are needed to be recorded and analyzed, including the presence and frequency of snoring episodes as one of the helpful markers, in order to diagnose obstructive sleep apnea.

Both obstructive and central sleep apnea are associated with increased morbidity and mortality. Sleep-disordered breathing can cause temporary elevations in blood pressure in association with lowered blood oxygen levels, and may cause elevated blood pressure during the day, and eventually, sustained high blood pressure (hypertension). The medical complications of sleep apnea are associated with an increased prevalence of hypertension, heart failure, myocardial ischemia and infarction, arrhythmias and sudden death, often related to the lack of oxygen (hypoxia) and the abrupt increases in sympathetic tone associated with repeated apneic episodes. Also, previously unsuspected sleep apnea may contribute to the apparent refractoriness of cardiac disease and inability to adequately treat heart failure. Other symptoms include cerebrovascular accident and arrhythmias. In addition, the daytime sleepiness or somnolence associated with untreated sleep apnea constitutes a hazard to the public health because of its implications for driving and the operation of industrial machinery.

These considerations combined with the availability of effective therapeutic techniques like continuous positive airway pressure (CPAP) and bi-level positive airway pressure (BIPAP) make it extremely important to detect sleep apnea and its complications accurately and confidently.

In the current state of the art, polysomnography is a well-established procedure to detect sleep apnea, but it is expensive and requires elaborate equipment and specially trained personnel. Therefore, it would be desirable to have a technique for detecting, differentiating and evaluating the cardiovascular effects of sleep apnea that is inexpensive, easy to use and that can be employed in a patient's home as well as in the hospital setting. The availability of such a convenient and cost-effective technique would make it possible to provide diagnostic evaluations for sleep apnea to many more patients than is currently feasible.

Furthermore, although traditional polysomnography provides detailed information about the various stages of sleep and wakefulness through brain activity (EEG) and eye movements (EOG), its ability to provide information about the cardiovascular complications of sleep apnea is extremely limited. This is especially important because of the inability of patients to report symptoms from events that occur during sleep. Therefore, furnishing objective evidence of previously unsuspected cardiovascular complications can alert physicians of the need to provide important treatment to patients who otherwise might not have received it.

The present invention is especially, though not exclusively, intended for both daytime and nocturnal monitoring applications. Preferably, it involves, combinationally, the cooperative, simultaneous "gathering", in addition to a number, such as three, "leads" of ECG data, heart sounds and several other categories, or facets, of mechanical anatomical, three-dimensional, vector data derived from a single, suitably anatomy-attached, three-orthogonal-axis accelerometer. This combination of ECG, and three-axis-accelerometer heart sound and additional anatomical data, allows readily for the confident detection and differentiation of sleep-disordered breathing.

In connection with practice of the present invention, the fact that what is proposed involves a three-dimensional vector method utilizing a three-axis accelerometer, is important for various reasons, including the conditions that chest and abdominal movements don't simply have a normal component (z axis only) to the chest, and that gravity and body position each influence these movements. As well, in this setting, such vector information is important to supply accurate magnitude information for respiration evaluation. Three-dimensional spatial directionality of such vector information is important also in obtaining, for evaluation use, body posture information from a subject.

A key element in this vector practice of the present invention centers on the true, multi-faceted use of a three-orthogonal-axis accelerometer to gather, in simultaneity, a large family of mechanical information from a subject, from, and in relation to, which information it is possible to analyze, interpret and display, accurate, related heart sound, respiratory, posture and body-activity data facets in order thereby to provide clinical experts with powerful evaluation and assessment insights into a subject's cardio-pulmonary condition for both acute and chronic kinds of situations.

In the preferred and best mode implementation of the invention, an accelerometer, placed preferably at, or very closely adjacent, the well-recognized V4, precordial ECG chest site, performs all signal data gathering, except for the gathering of ECG electrical information which also plays a role in the practice of the invention. However, in some cases, it may be useful to employ an independent microphone for sound-collecting purposes. Such an independent microphone could be either a physically and spatially independent device, or it could be physically "package-integrated" with the employed accelerometer.

Given the state of the art today involving the making of extremely tiny mechanical and electromechanical structures, a three-orthogonal-axis accelerometer of the kind which is usable conveniently in the practice of the present invention, referred to also herein simply as a three-axis accelerometer, might typically have dimensions on the order of about 5×5×2-mms. Such a device might be "stand-alone" in nature, limited just to the basic acquisition of three-axis signal data, or it might be structured in combination (internally in an integrated package) with relevant, appropriate, algorithmically programmed, signal-data-processing and recording micro-circuitry, either "structural approach", of course, coming with appropriate, readily externally accessible, signal-output connection structure(s).

In this connection, it will be immediately apparent to those skilled in the art that such an accelerometer, as well as all, appropriate signal-data-processing circuitry, including digital computer data-processing and recording circuitry, and algorithmic methodology (as such are described functionally and organizationally below both in high-level text and in block/schematic drawing form) needed to implement the data-handling processing and analyzing aspects of the invention, may be conventional in nature, and may take on a number of different, entirely adequate forms. The details of these matters do not form any part of the present invention, and they are, accordingly, not discussed or elaborated herein in great detail. Rather, they are mentioned in the practice of the invention, as just suggested, in appropriate, high-level disclosure terms.

Useful background information regarding such data-processing and algorithmic circuitry and methodology employing digital computer structure may be found in the following documents, the entire contents of which are hereby incorporated herein by reference: U.S. Pat. No. 7,096,060 to Arand et al., issued Aug. 22, 2006, for "Method and System for Detection of Heart Sounds"; U.S. Patent Application Publication No. 2007/0191725 of Nelson, published Aug. 16, 2007, for "Wavelet Transform and Pattern Recognition Method for Heart Sound Analysis"; and U.S. Patent Application Publication No. 2010/0094148 of Bauer et al., published Apr. 15, 2010, for "Differential Apneic Detection in Aid of Diagnosis and Treatment". Signal-processing algorithmic methodology and other relevant matters described in these documents may be employed very satisfactorily in the signal-processing and data handling and analyzing environment associated with practice of the present invention.

Preferably, the main signal-gathering device, the three-axis accelerometer, will be located on the subject's chest in a position on the thorax, such as the one mentioned above, so it can easily pick up respiratory movement. Acquired data may be recorded onto associated digital media, such as onto an accelerometer-package-integrated SIM chip similar to those used in digital cameras, with such data being easily downloadable to an external computer.

According to a preferred and best-mode manner of describing the present invention, it proposes a method for monitoring sleep-disordered breathing including the steps of (a) collecting, simultaneously, multi-facet, three-axis data from a sleeping subject utilizing an anatomy-attached, three-orthogonal-axis accelerometer, and (b) following such collecting, processing and analyzing the collected data to detect associated, disordered breathing including assessing the presence of at least one of (a) sleep-disordered breathing generally, (b) sleep apnea specifically, (c) differentiation between central and obstructive sleep apnea, and (d) hypopnea.

The invention may also be expressed as a method for detecting sleep disordered breathing involving (a) using a three-orthogonal-axis accelerometer attached to a selected site on a subject's anatomy, collecting from that site, over a chosen, or selected, time interval, multi-facet, three-axis accelerometer signal data which may include, as collected components, two or more of activity, posture, heart sounds, snoring, and respiration, (b) independently facet-filtering this collected data through one or more independent, facet-specific filtering agencies which produce, respectively, filtered data reflecting, and specific to, one or more of the mentioned components, (c) selectively and combinationally processing and analyzing such filtered data, and (d) from the steps of processing and analyzing, producing output information associated with the selected anatomical site describing any detected sleep disordered breathing.

Added as steps to these representative, methodologic characterizations of the invention in a further embodiment are the additional steps of (a) simultaneously acquiring, during a chosen time interval such as the one mentioned above, ECG electrical data, and (b) including information contained in such acquired electrical data in the mentioned processing and analyzing steps.

Further included in the implementation of the present invention may be the practice, based upon the analyzing step, of producing, as output, at least presentable graphics information relating to at least one of (a) sleep-disordered breathing generally, (b) sleep apnea specifically, (c) differentiation between central and obstructive sleep apnea, and (d) hypopnea.

These and other important features and advantages of the invention will become more fully evident as its detailed description which follows shortly is read in conjunction with the accompanying drawings.

DESCRIPTIONS OF THE DRAWINGS

FIG. 1, which is to be viewed in two different manners for explaining the present invention, is, generally speaking, a block/schematic diagram which illustrates, in a preferred and best-mode manner, both the basic methodology of the present invention (in both of its functional appearances), and a system for performing it. More particularly, this figure presents a stylized, schematic illustration picturing a fragmentary portion of an anatomical setting regarding which two, different, broad-level implementations, or modifications, of the invention are shown. In one of these implementations, a single, three-orthogonal-axis accelerometer is attached at an appropriate, stabilized anatomical location to the outside of the anatomy. In the other, a single, internal, implanted accelerometer is employed.

In this figure, only the first-mentioned accelerometer i.e., the single, external accelerometer, is represented by a block in the figure. The other, internal, implanted accelerometer is simply represented by a darkened cross mark.

Figure 2:
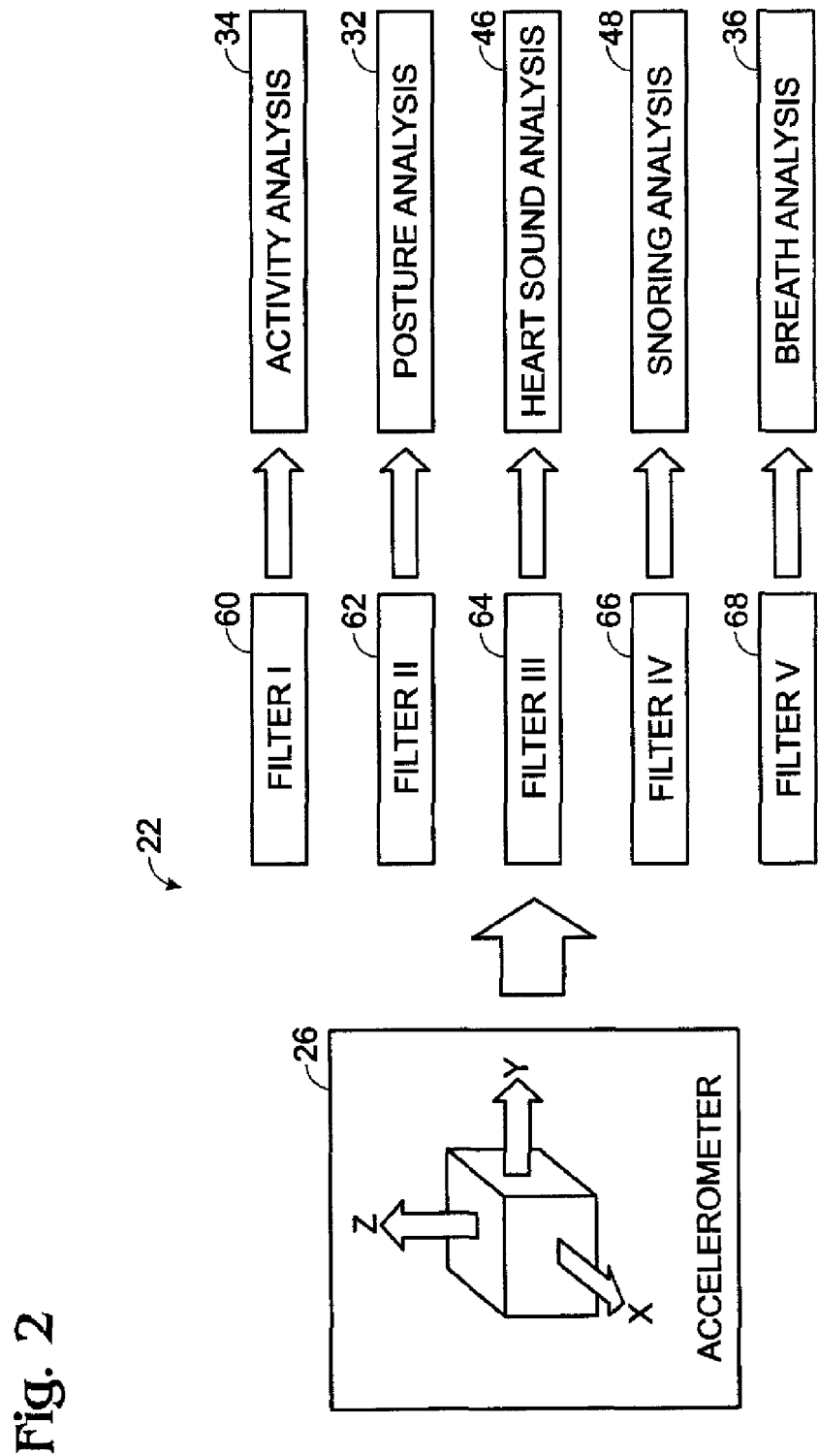

FIG. 2, which links with FIG. 1 as will shortly be explained, is another block/schematic diagram, here picturing a single, three-orthogonal-axis accelerometer operationally posed in relation to five, signal-data, facet-specific, filtering agencies, and five, respectively associated data analysis agencies, which, in the practice of the invention, filter, process and analyze three-axis accelerometer data relating to subject activity level, posture, heart sounds, snoring and respiration.

FIGS. 3-9, inclusive, offer several, graphical, actual display-screen presentations, based upon experimental practice tests of the invention, variously showing collected, filtered, processed and analyzed vector-mechanical (accelerometer) and ECG electrical information and data, extending over a selected interval of time embracing a plurality of cardiac cycles.

Figure 3:
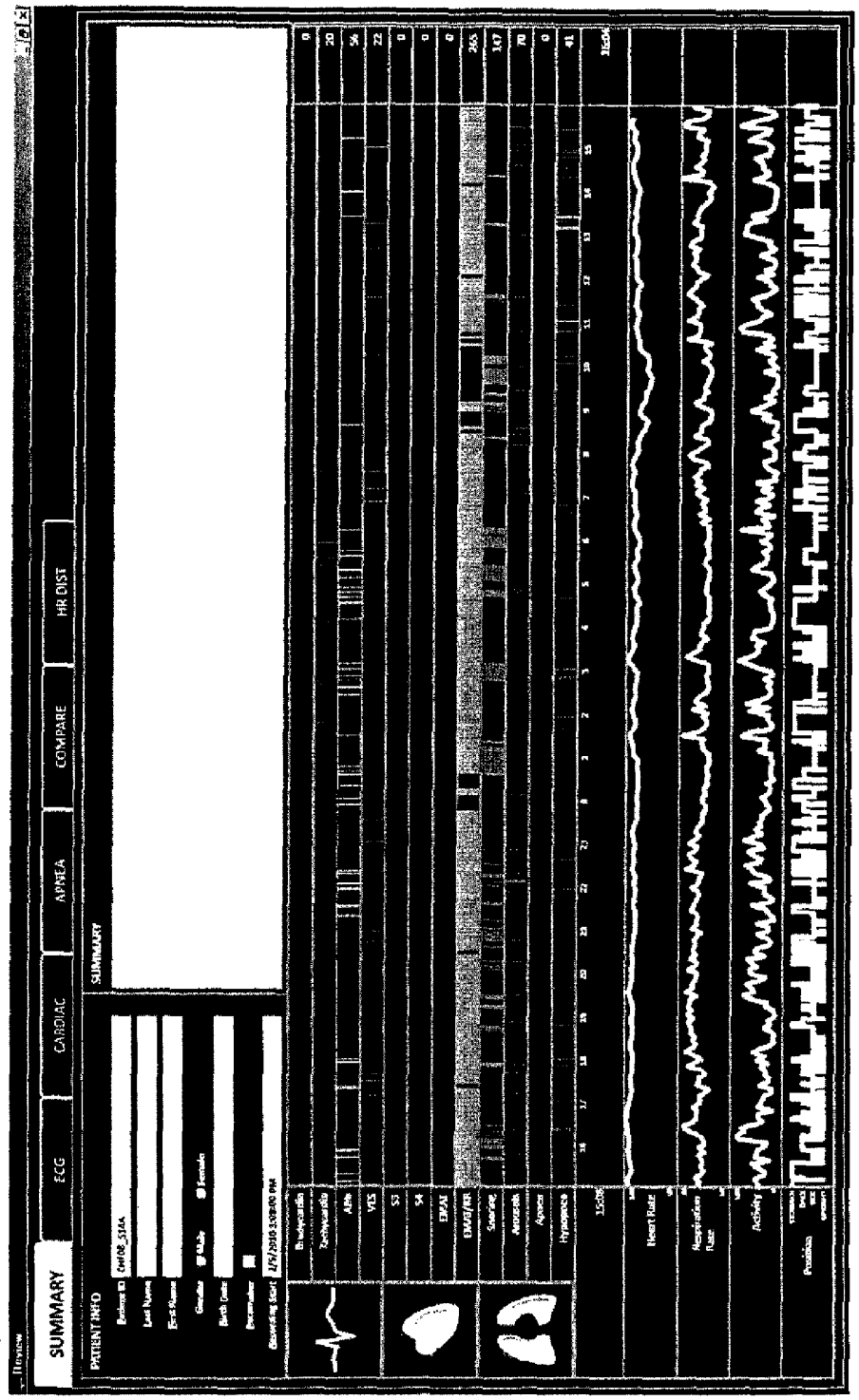

FIGS. 3-6, inclusive, are in the nature of actual output reports—FIG. 3 having the nature of a major, overall analysis-summary report, and the other three figures showing selected aspects of (or leading to) that summary report. In FIG. 3, the lower, left-hand column, from top to bottom, identifies the following, seventeen topics, known to those skilled in the art as: Bradycardia, Tachycardia, Afib, VES, S3, S4, EMAT, EMAT/RR, Snoring, Arousals, Apnea, Hypopnea, "11:26" (a time stamp for the presented data, Heart Rate, Respiration Rate, Activity, and Position (STOMACH, BACK, SIDE, UPRIGHT).

In the listing above of "topic", it may be useful here to include definitions for several, as follows:
- VES—Ventricular extrasystole.
- S3—The third heart sound, associated with an abnormal diastolic filling pattern, the most likely explanation for which is that vigorous and excessively rapid filling of blood into a stiff ventricle is suddenly halted, causing audible vibrations.
- S4—The fourth heart sound—a sound which occurs after T-wave onset and before the first heart sound in a cardiac cycle, occurring as blood enters a relatively non-compliant ventricle late in diastole because of atrial contraction, resulting in vibrations of (a) the left ventricular muscle, (b) the mitral valve structure, and (c) the left ventricular blood mass often associated with left ventricular hypertrophy due to the decreased compliance and frequency present in acute myocardial infarction.
- EMAT—The electromechanical activation time measured from Q-wave onset (from ECG information) to the time of closure of the mitral valve within the first heart sound. The time value of EMAT reflects the time required for the left ventricle to generate sufficient force to close the mitral valve, and is therefore related to the acceleration of the pressure curve in the left ventricle.
- EMAT/RR—The ratio of EMAT divided by the duration from an R-peak time to the next successive R-peak time.

Figure 4:
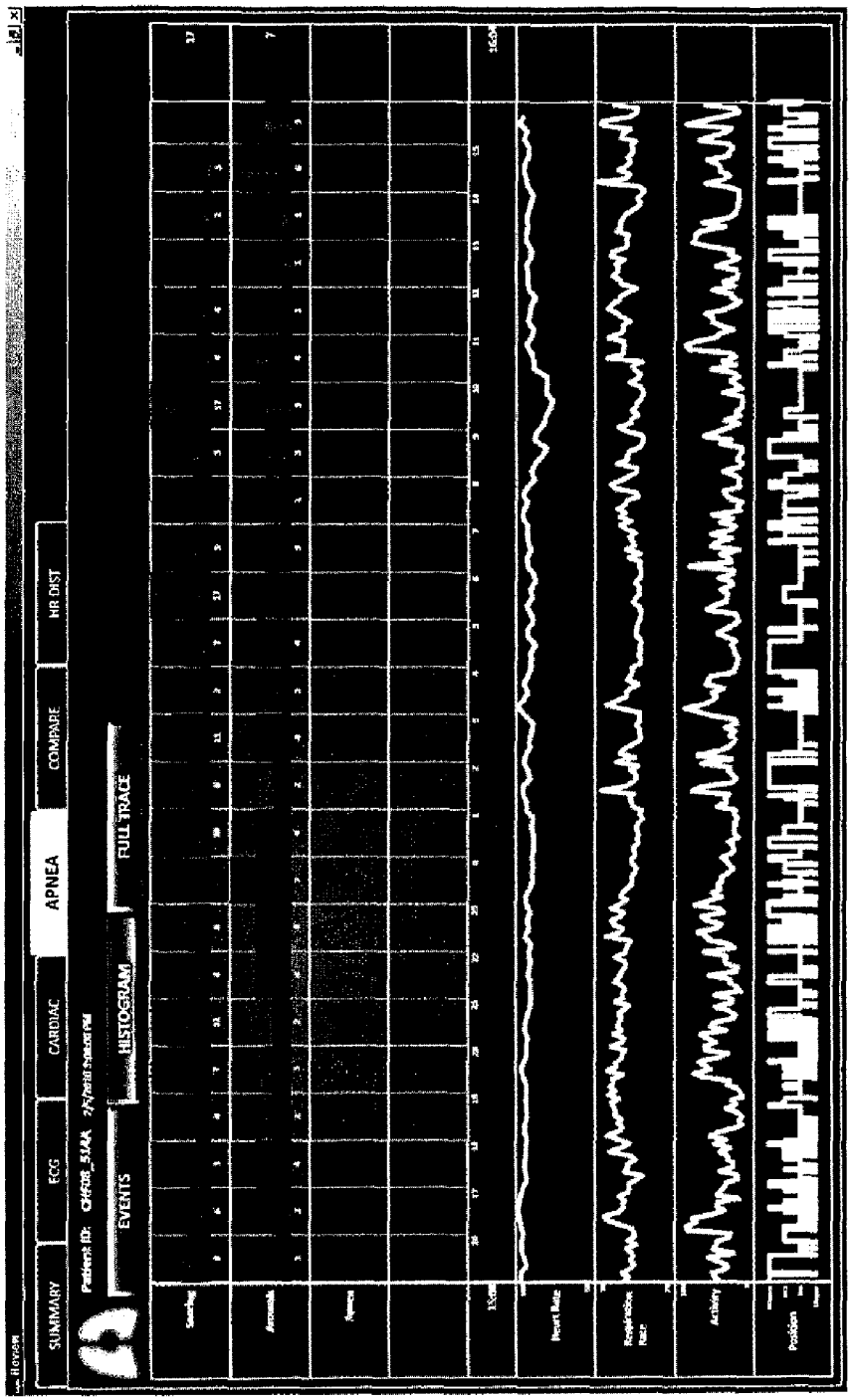
Figure 5:
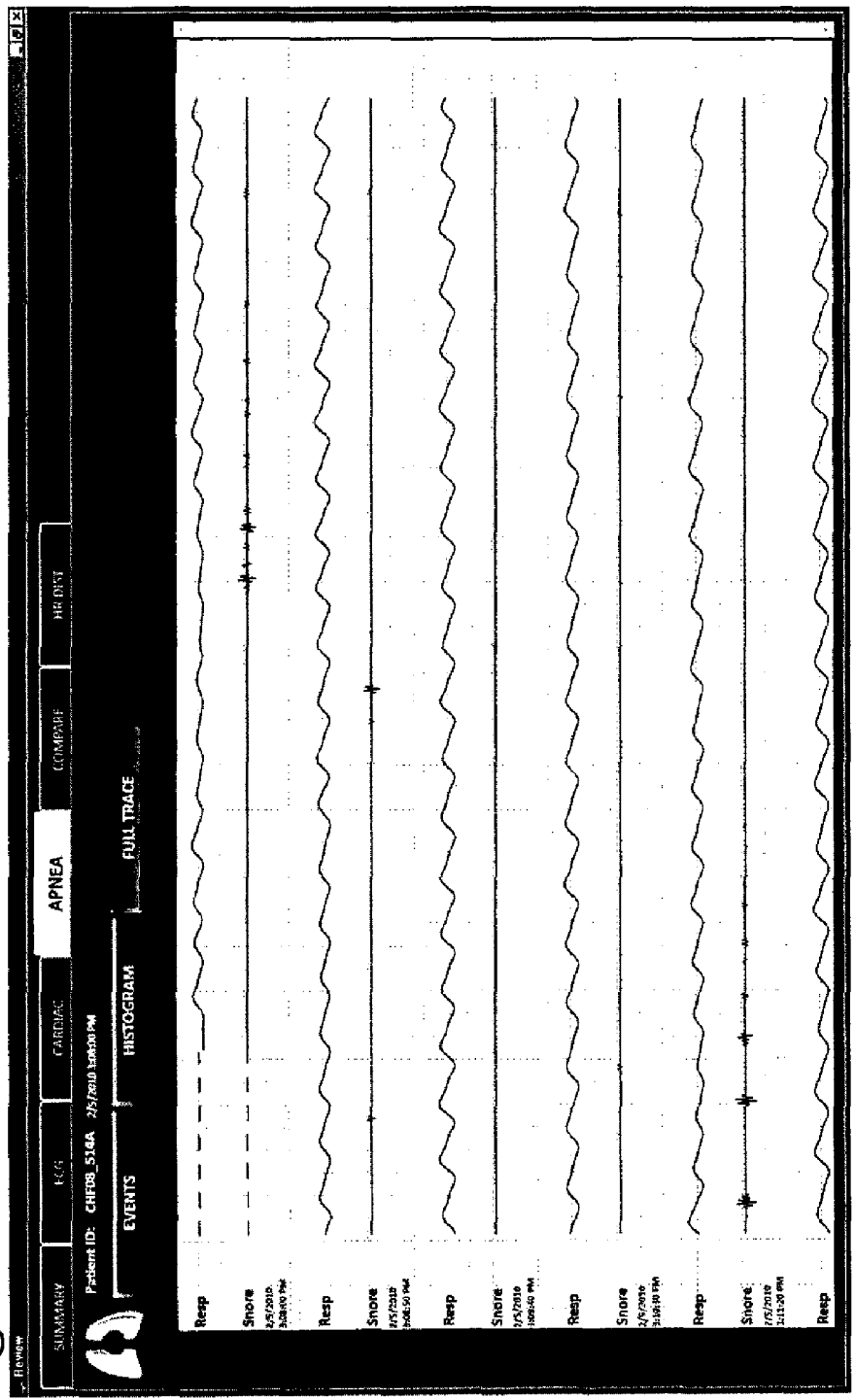
Figure 6:
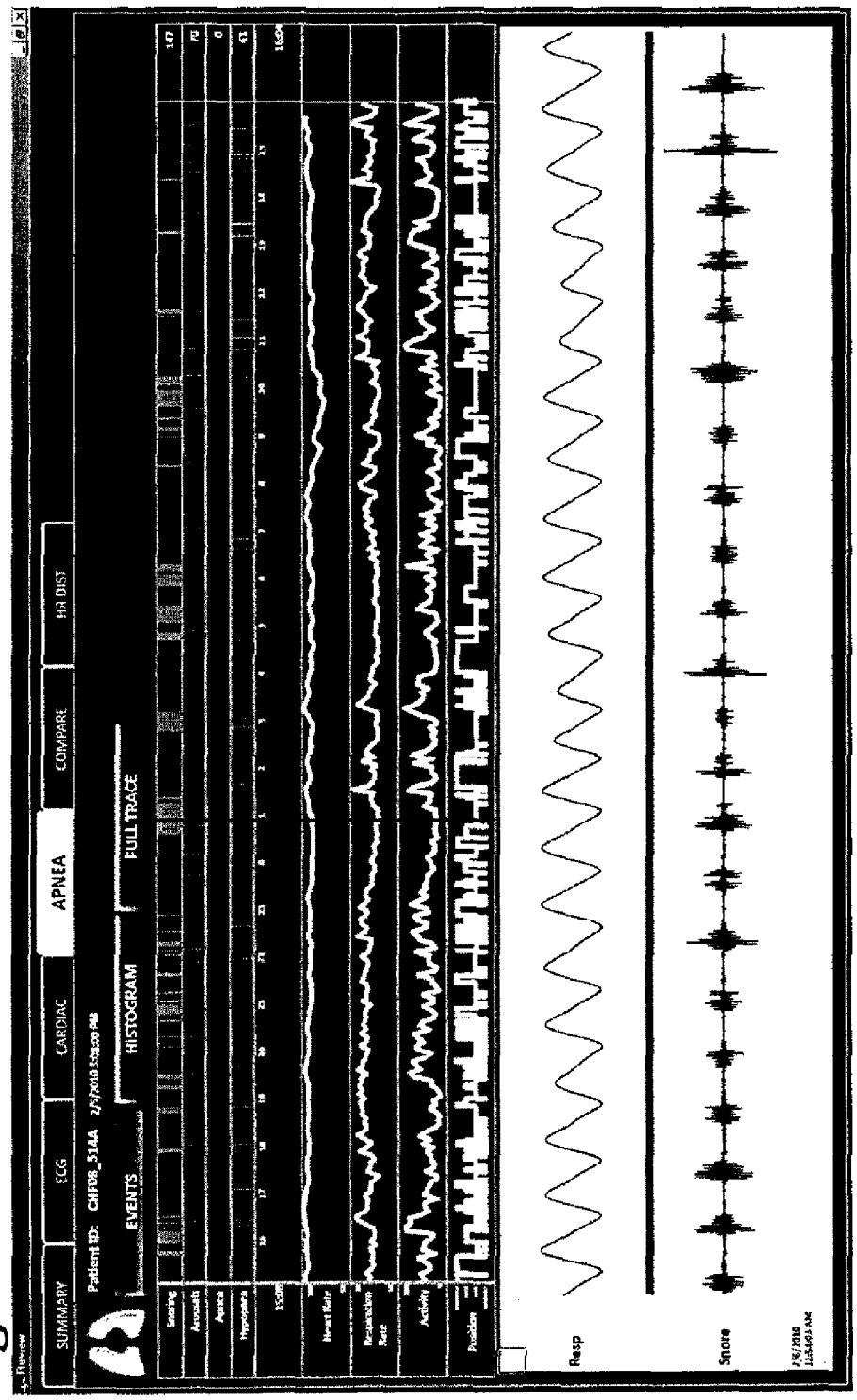

FIGS. 4, 5 and 6 focus attention on selected features of detected apnea: Histogram (FIG. 4), Full Trace (FIG. 5) and Events (FIG. 6), respectively.

Figure 7:
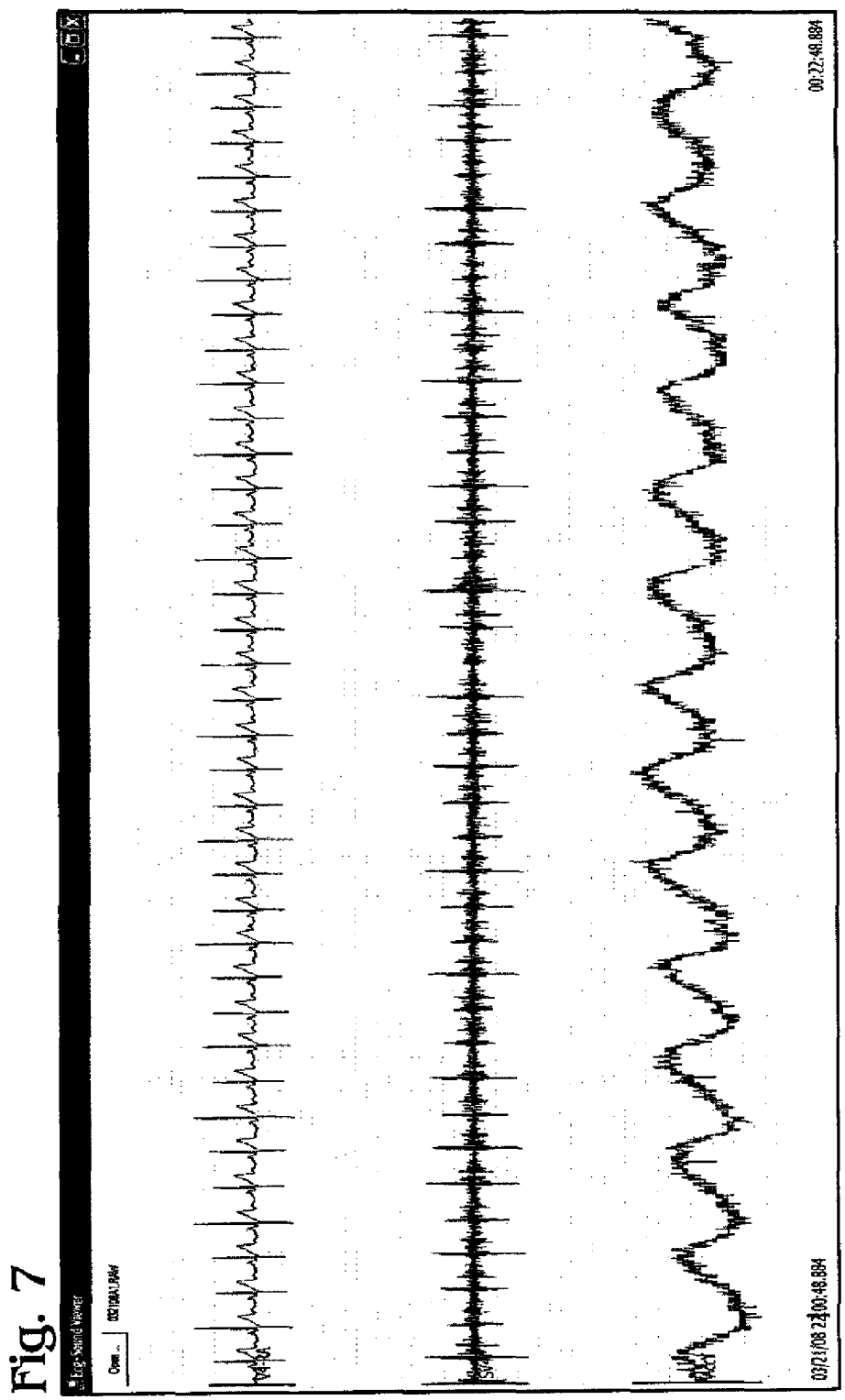
Figure 8:
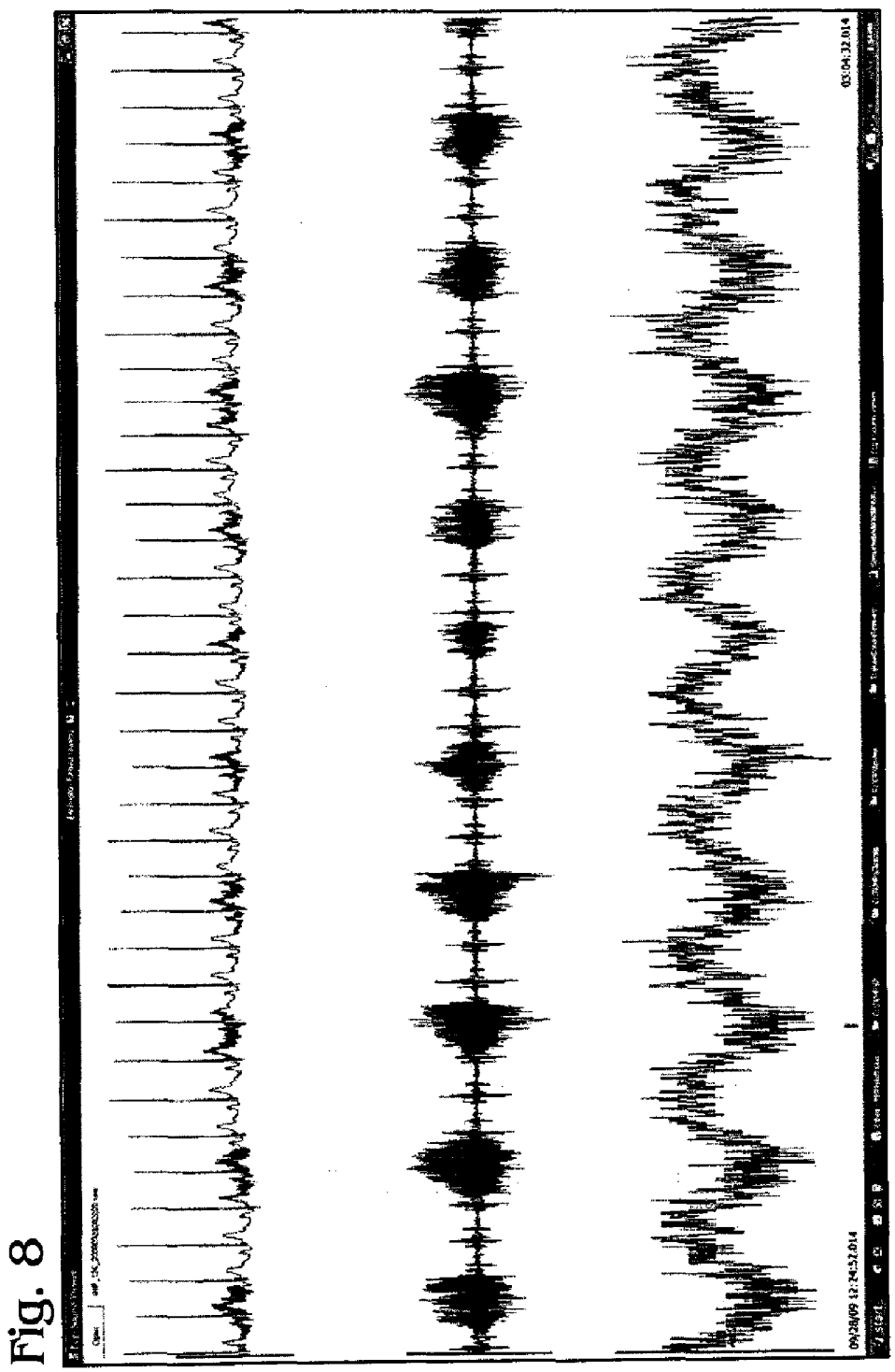
Figure 9:
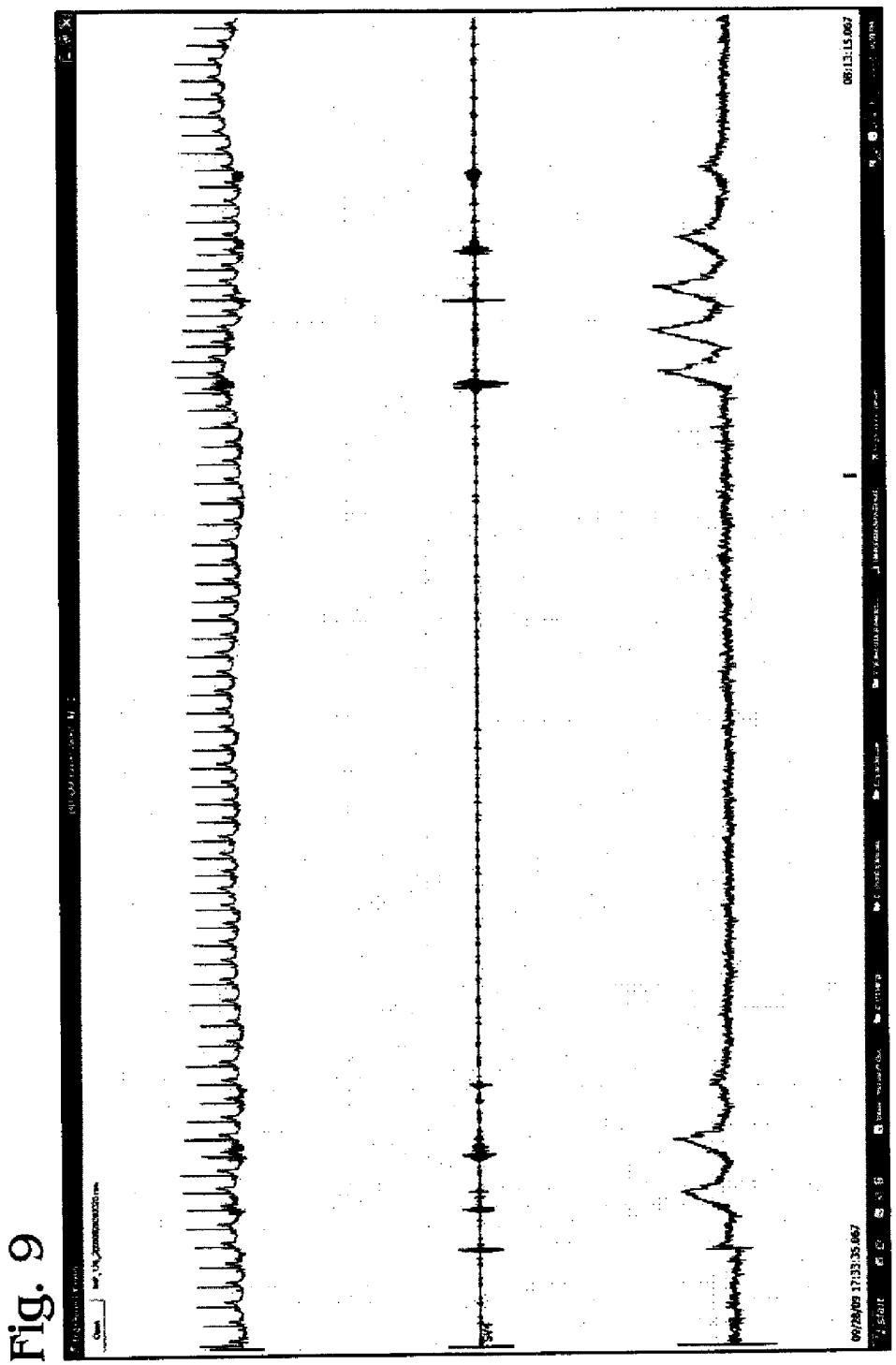

FIGS. 7-9, inclusive, picture specifically information gathered from a subject during three, different, breathing-characteristic episodes—FIG. 7 showing, progressing downwardly through this figure, ECG, sound and direct-from-accelerometer signals during normal breathing, FIG. 8, also so downwardly progressing, showing the same signals during a period of normal breathing with repetitive snoring, and FIG. 9 presenting the same three signals, but here illustrating an example of an obstructive apneic event. (Central apneas are defined as periods of apnea with no snoring detections).

Timing information comes from the evident, simultaneously acquired, and thereafter conventionally marker-event processed, three-lead, ECG electrical data.

The report information presented in FIGS. 3-9, inclusive, and the various manners shown for presenting it, are basically conventional, and very familiar to those skilled in the relevant medical art, and therefore do not require elaboration in this text. The specific content and format of these reports, of course, does not form any part of the present invention. What is important in relation to the practice of the present invention is (1) that this content has been gathered in a multifaceted, simultaneous fashion, and (2), has been so gathered, insofar as the anatomical mechanical data is concerned, in a three-dimensional vector manner to provide three axis magnitude and directional information, either externally or internally relative to a subject's anatomy.

DETAILED DESCRIPTION OF THE INVENTION

Turning now to the drawings, and referring first of all to FIGS. 1 and 2, indicated generally at 20 in FIG. 1 is a largely self-explanatory, high-level, overall, block/schematic diagram fully illustrating the structure, and the methodologic implementation, of two preferred and best-mode embodiments of, and manners of practicing, the sleep disordered breathing-monitoring practice of the present invention. FIG. 2, which is also very self-explanatory, illustrates at 22 another high-level block/schematic diagram which pictures individual data-component (individual facet) filtering which takes place within a portion of what is shown in FIG. 1 in accordance with practice of the invention. More will be said shortly about the disclosure relationship of these two drawing figures.

FIG. 1, in particular, presents a stylized, schematic illustration of a fragmentary portion of a subject's anatomy in a setting regarding which the present invention is to be practiced. Even more particularly, and as was mentioned briefly above, FIG. 1 pictures two, different, broad-level implementations, or modifications, of the invention.

As earlier stated, in the preferred implementation where a single, external, three-orthogonal-axis accelerometer is to be employed, such an accelerometer is preferably attached in a stabilized condition at the V4 anatomical location to the outside of the subject's chest—here shown by a line 24. Such a single accelerometer in FIG. 1 is represented by block 26.

In the second preferred implementation of the invention, a single, implanted internal accelerometer is suitably installed inside the anatomy at an appropriate location, such as that marked by a small, darkened cross mark 30, adjacent and above the subject's heart (not shown).

Preferably, though not necessarily as has already been pointed out, all relevant, anatomical, mechanical activities, including heart sound events, are captured/collected directly by the employed accelerometer. The two embodiment-illustrations presented in FIG. 1, at least as they may initially be thought about, are intended to reflect this "all-mechanical-events-collection" use of an accelerometer. As was mentioned earlier, it may be desirable in certain instances, with respect to an externally employed accelerometer, to employ, either directly associated in a package with it, or as an independent device closely adjacent it, an independent microphone. Those skilled in the art will immediately understand how to implement such a variation of the invention which is not specifically pictured in the drawings herein.

Operatively connected by various information-, and data-processing, flow lines that are evidenced in FIG. 1 are various, other, text-labeled blocks which, collectively with the data- and signal-flow lines presented in this figure, describe the systemic structure and methodologic operation of the present invention. More specifically, included as shown, directly connected to accelerometer 26, are a block 32, labeled Body Posture Detection, a block 34, labeled Activity Level, a block 36, labeled Breath Detection, and a block 38, labeled Acoustic Signature Filter and Analysis. Additionally pictured, but not connected to the accelerometer, is a block 40, labeled Multiple Lead ECG Input. Further shown, either indirectly connected to the accelerometer, or directly connected in a flow path leading from block 40, are a final-output, analysis-summarizing block 42, labeled Sleep Summary, a block 44, labeled Wake Summary, a block 46, labeled Heart Sound Measurements, a block 48, labeled Snore Sound Detection, a block 50, labeled R-wave Detection, a block 52, labeled Hypopnea/Apnea Detection, and a block 54 labeled ECG Measurements: Timing Morphology.

The data and signal-flow connections which interconnect these blocks are clearly indicated by arrow-headed lines. A dual-illustration-purpose bracket 56 which appears horizontally adjacent the bottom of FIG. 1 represents either an included, or an external, suitably algorithmically programmed digital computer. This computer, whereby appropriate signal processing and data analyzing take place, if "internal", simply means that its various data-handling features that are relevant to the operations of certain ones of the above-identified blocks are incorporated in those blocks, or if "external", means that there are appropriate operative connections between the relevant blocks and the associated, external computer. Appropriate algorithmic, data-handling programming and processing, per se, may be entirely conventional, are well within the skill and knowledge of those generally skilled in the relevant art, do not require detailed elaboration herein, and may be guided effectively and very satisfactorily by the disclosure contents of the above-referenced, prior art documents.

Not conventional, of course, is that all relevant data involved in the practice of the invention is collected simultaneously, with all of that collected data (except where a microphone is employed which is not the case in the preferred practice of the invention) which is mechanical in nature being collected three-dimensionally in order to establish extremely useful spatial vector magnitude and directionality information that leads to a notably higher-than-conventional quality-level of sleep disordered assessment capability in the "hands" of skilled medical personnel.

As a final mention of structure which is illustrated in FIG. 1, block 40, which represents a conventional, multiple-lead ECG structure is suitably and conventionally connected to the subject's anatomy, as indicated by a broad, darkened, upwardly pointing arrow 58 in this figure.

Within the collection of blocks presented in FIG. 1, we here mention the basic involvements of several. Activity Level block 34 relates generally to a subject's physical activity as measured by a three-axis accelerometer, throughout the day, expressible by a parameter ranging from 0% to 100%. Wake Summary block 44 identifies those times during a subject-recording-period wherein he/she was awake or asleep. Sleep Summary block 42, a key output-information block, pointedly identifies to identify abnormal breathing findings during a subject's sleep time—i.e., the presences and durations of all relevant categories of sleep disordered breathing. It is from this block (under computer control) that much of the information seen in the illustrations furnished in several of FIGS. 3-9, inclusive, is presented for medical-expert appraisal.

Turning attention now to the contents of FIG. 2 in the drawings before discussing its linkage with FIG. 1, the schematic arrangement (previously mentioned) which is generally illustrated at 22 is specifically pictured in this figure including, adjacent its left side, the same, single accelerometer 26 which is pictured in schematic block form in FIG. 1. Adjacent the right side of FIG. 2 is a vertical stack of five blocks which directly relate, progressing downwardly through this stack in the figure, to previously mentioned blocks 34, 32, 46, 48 and 36. Accordingly, these five blocks have been identified with the same, five, respective reference numerals. As can be seen, these five blocks, in a the "downward-reading" order of them just indicated, are text labeled, respectively, Activity Analysis, Posture Analysis, Heart Sound Analysis, Snoring Analysis, and Breath Analysis.

In FIG. 2, operatively interposed, in a data-flow manner, accelerometer 26 and the five "Analysis" blocks which have just been mentioned, are five, independent, appropriately algorithmically controlled, facet-specific, signal filters represented by five blocks which are pictured at 60, 62, 64, 66 and 68. These five filter blocks are labeled, respectively, Filter I, Filter II, Filter III, Filter IV and Filter V. Data-flow arrows, not specifically labeled, furnish operative data-flow connections extending appropriately toward the right from accelerometer 26 to the stack of blocks pictured at the right side of FIG. 2.

In relation now to the connection which exists between FIGS. 1 and 2, the signal data filtering arrangement which is pictured in FIG. 2 may either be interpreted to describe (1) an arrangement wherein there are indeed, free-standing independent filters that operate upon accelerometer data to apply conventional signal filtering so that the blocks to which they feed information receive only that information relevant to what that block is to handle, or (2) an arrangement wherein independent filtering takes place with the "contents" of blocks 60, 62, 64, 66, 68 effectively taking the form of computer-based circuitry and algorithmic programming which is resident within each one of the respectively associated analysis blocks.

It makes no difference from the standpoint of the ultimate operation and practice of the present invention which of these conditions is selected for implementation in a system designed to carry out and enable the practice of the present invention. What is important, regarding filtering, is that three-axis vector data acquired by accelerometers, such as by accelerometer 26, will be adequately filtered so that only the appropriate data for each of the five, different analysis blocks ultimately gets supplied to that block. How such filtering is designed to accomplish this is entirely conventional in nature, and is well within the skill and understanding of those generally skilled in the relevant art.

Still staying principally with a description of the methodology of the invention in the context of employing a single, externally utilized, anatomy-attached accelerometer, in the implementation of the invention, such an accelerometer is suitably anchored (as already mentioned) to, preferably, the V4 anatomical site using any conventional device-attachment methodology, such as one of the methodologies typically employed to attach the contact ends of conventional ECG leads. Additionally, an appropriate, plural-lead set (such as a three-lead set) of ECG conductors is attached to the anatomy as generally, suggestively indicated by previously mentioned arrow 58.

Assuming that all data-processing, filtering and calculating, etc. will be performed by digital computer circuitry which is not included within the directly anatomy-attached accelerometer device, suitable connection structure provider therefor is coupled to an appropriately programmed, independent digital computer, such as the one represented by previously described bracket 56 in FIG. 1, with that computer being armed algorithmically to perform all of the data-processing, data-analyzing and assessing functionalities required ultimately to generate output information such as that presented graphically in FIGS. 3-9, inclusive. As has been mentioned several times herein, such algorithmic programming may be designed in a number of different conventional ways, several of which are fully described in the several prior art documents which have been referenced in the text above herein.

With the systemic structure that has just been described appropriately connected to a subject, and with this equipment in a condition ready to function, data in a multifaceted sense is collected simultaneously during the one or more selected time intervals. These intervals may be relatively close together, or they may be separated by fairly long periods of time, recognizing, of course, that a long-term separation will most probably necessitate disconnection and later reconnection of the anatomy attached equipment.

The data collected includes mechanical, three-dimensional vector data acquired from the attached accelerometer, and ECG electrical data acquired from the attached ECG structure. Mechanical data so acquired includes the facets of a subject's body position (or posture), respiration activity, basic physical activity level, heart-produced sound information, including the classic heart sounds and murmur, and, of course, electrical data includes the collected ECG information.

FIG. 1 in the drawings illustrates the flow of collected and processed data which now takes place with respect to that which is "simul-collected" during the mentioned one or several, selected time intervals. With regard to collected mechanical data, this is filtered appropriately so that only that mechanical data which relates correctly to each of the relevant facet categories of such data involved in the practice of the invention makes its way to the appropriate analysis "portion, or region," of the invention. Mechanical data so filtered and directed appropriately is vector calculated to determine spatial vectors that give three-axis magnitude and directionality information, and collected ECG information is processed in accordance with the task indications provided in the labeling of blocks 50, 54 in FIG. 1. Such ECG-related data is employed, among other reasons, for furnishing appropriate timing information useful in relation to what ultimately gets presented, in an output sense, to skilled medical personnel.

Blocks 42, 52 in FIG. 1 develop comprehensive sleep disordered breathing data, as indicated in their respective labelings, to produce, and thereby make available to skilled medical personnel, time-based, processed and analyzed sleep disordered breathing information, such as that presented in great detail in the several graphical images included in drawing FIGS. 3-9, inclusive. And, as can readily be seen from these seven drawing figures, furnished indeed is a rich literature of sleep disordered, and tangentially other, information.

It should now be apparent how what has just been described principally in conjunction with the employment of a single, external accelerometer may be modified appropriately to fit with the other, single-accelerometer implanted internal implementation style of the invention described earlier herein.

It should also now be completely evident, from the a reading of the descriptive material provided hereinabove, taken along with a view of the several drawings figures, exactly how the methodology of the invention may be performed, and how a system to implement this methodology in the hands, and under the control, of, for example, a skilled medical person, may be accomplished. Great value is furnished to such a skilled person by virtue of the fact, and really by virtue of two facts, that all data, mechanical and electrical, are acquired simultaneously throughout one or more selected time intervals. Acquired electrical ECG information furnishes, among other things which are evident from the contents of drawing FIGS. 3-9, inclusive, important timing information which is useful in relation to the various categories and facets of mechanical information derived from accelerometers. Conventionally performed vector calculations with respect to each of the multi-faceted, collected mechanical data categories produces extremely useful three-axis magnitude and directionality information which furnishes a skilled medical person with a high-level capability for analyzing and assessing a subject's sleep disordered condition, if one exists.

It will be very evident from the contents of the graphical presentations in FIGS. 3-9, inclusive, that a very wide range of simultaneously collected, processed and analyzed information, characterized in a number of different useful ways, may be called for and presented in accordance with practice of the present invention. While much summary information is of course callable from Sleep Summary block 42, it will be evident to those skilled in the art, inasmuch as digital computer circuitry is involved, that data at various different operational levels within the practice of the invention may be called forth, for example, from other ones of the blocks presented in FIG. 1 to furnish graphical output data, such as that which is evidently presented in certain ones of the just-identified, several, graphical drawing figures.

Accordingly, while a preferred and best-mode embodiment, and two important preferred and best-mode modifications, of the methodology of the present invention have been illustrated and described herein, we appreciate that variations and modifications not expressly presented herein may come to the minds of those generally skilled in the art, and it is our intention that the following claims to invention will be interpreted to cover all such variations and modifications.

We claim:

1. An external-only method for detecting and differentiating a sleeping subject's manifestations of sleep-disordered breathing comprising
    attaching a single, three-axis accelerometer to a subject's chest,
    acquiring data from the three axis accelerometer during a subject-recording period,
    identifying, based on accelerometer data, sleep times during the subject-recording period when the subject is asleep, and generating, based on accelerometer data, a wake summary,
    during the identified sleep times, utilizing solely the attached accelerometer, simultaneously collecting, externally-only, sleeping-subject-specific, three-axis, vector-mechanical accelerometer data,
    filtering the accelerometer data through five independent facet-specific signal filters outside the subject to generate components specific to (a) heart sounds, (b) body position, (c) body activity, (d) snoring, and (e) chest-movement-based respiration,
    collecting sleeping-subject-specific ECG data outside the subject, and
    generating a sleep summary based on the wake summary including processing and analyzing the components of the accelerometer data and the ECG data outside the subject, to detect and differentiate the presences of (a) sleep-disordered breathing generally, (b) sleep apnea generally, (c) differentiated central and obstructive sleep apnea specifically, and (d) hypopnea specifically.

2. The external-only method of claim 1, wherein attaching a single, three-axis accelerometer to a subject's chest is adjacent a V4, precordial ECG site.

* * * * *